United States Patent
Lee et al.

(10) Patent No.: US 9,880,408 B2
(45) Date of Patent: Jan. 30, 2018

(54) SUBSTRATE INSPECTION DEVICE AND METHOD

(71) Applicants: BOE TECHNOLOGY GROUP CO., LTD., Beijing (CN); HEFEI XINSHENG OPTOELECTRONICS TECHNOLOGY CO., LTD., Hefei, Anhui (CN)

(72) Inventors: Yongjin Lee, Beijing (CN); Unsub Lee, Beijing (CN); Tae Hyuck Yoon, Beijing (CN)

(73) Assignees: BOE TECHNOLOGY GROUP CO., LTD., Beijing (CN); HEFEI XINSHENG OPTOELECTRONICS TECHNOLOGY CO., LTD., Hefei, Anhui (CN)

(*) Notice: Subject to any disclaimer, the term of this patent is extended or adjusted under 35 U.S.C. 154(b) by 76 days.

(21) Appl. No.: 14/895,703

(22) PCT Filed: Jul. 17, 2015

(86) PCT No.: PCT/CN2015/084373
§ 371 (c)(1),
(2) Date: Dec. 3, 2015

(87) PCT Pub. No.: WO2016/095517
PCT Pub. Date: Jun. 23, 2016

(65) Prior Publication Data
US 2016/0363791 A1 Dec. 15, 2016

(30) Foreign Application Priority Data
Dec. 18, 2014 (CN) .......................... 2014 1 0803896

(51) Int. Cl.
*H04N 7/18* (2006.01)
*H04N 1/14* (2006.01)
(Continued)

(52) U.S. Cl.
CPC ....... *G02F 1/1309* (2013.01); *G01N 21/8806* (2013.01); *G01N 21/95* (2013.01);
(Continued)

(58) Field of Classification Search
CPC .. H04N 7/18; H04N 1/14; H04N 3/02; H04N 9/10
(Continued)

(56) References Cited

U.S. PATENT DOCUMENTS 5,311,276 A 5/1994 Masao et al.
2003/0174214 A1 9/2003 Shin et al.
(Continued)

FOREIGN PATENT DOCUMENTS

CM 104391390 A 3/2015
CN 1445532 A 10/2003
(Continued)

OTHER PUBLICATIONS

Machine Translation of JP 2009-115479, "Inspection Device", Kobayashi Shigeki, May 28, 2009.*
(Continued)

*Primary Examiner* — Daquan Zhao
(74) *Attorney, Agent, or Firm* — Ladas & Parry LLP; Loren K. Thompson

(57) ABSTRACT

A substrate inspection device and method are disclosed. The substrate inspection device includes a conveyance stage for carrying the substrate on its surface; a region scanning camera located at a first side of the conveyance stage, provided to be opposite to the surface, and configured for inspecting standard specification of the substrate; a line scanning camera located at the first side of the conveyance stage, provided to be opposite to the surface, and configured for inspecting edge line and size of the substrate; and a light source located at a second side of the conveyance stage
(Continued)

opposite to the first side, configured for irradiating light rays onto the substrate, so as to be utilized by the region scanning camera and the line scanning camera for inspecting the substrate.

15 Claims, 4 Drawing Sheets

(51) Int. Cl.

| | | |
|---|---|---|
| *H04N 3/02* | (2006.01) | |
| *G02F 1/13* | (2006.01) | |
| *G01N 21/95* | (2006.01) | |
| *G06T 7/00* | (2017.01) | |
| *H04N 5/225* | (2006.01) | |
| *G01N 21/88* | (2006.01) | |
| *H04N 9/10* | (2006.01) | |

(52) U.S. Cl.
CPC ......... *G06T 7/0006* (2013.01); *H04N 5/2256* (2013.01); *H04N 7/18* (2013.01); *G01N 2021/9513* (2013.01); *G06T 2207/10004* (2013.01); *G06T 2207/30121* (2013.01)

(58) Field of Classification Search
USPC .............................................. 348/92, 61, 98
See application file for complete search history.

(56) References Cited

U.S. PATENT DOCUMENTS

| | | | | |
|---|---|---|---|---|
| 2012/0184086 | A1* | 7/2012 | Yang | ................. H01L 21/67092 |
| | | | | 438/464 |
| 2015/0374557 | A1* | 12/2015 | Varga | ................. A61F 13/15772 |
| | | | | 382/103 |

FOREIGN PATENT DOCUMENTS

| | | | | | |
|---|---|---|---|---|---|
| CN | 1537227 | A | | 10/2004 | |
| CN | 201311924 | Y | | 9/2009 | |
| CN | 103913468 | A | | 7/2014 | |
| JP | 2009115479 | A | * | 5/2009 | ........... G01N 21/956 |
| JP | 2011-052967 | A | | 3/2011 | |
| KR | 1020060039516 | A | | 5/2006 | |
| KR | 20090078566 | A | | 7/2009 | |
| KR | 100963603 | B1 | | 6/2010 | |

OTHER PUBLICATIONS

First Chinese Office Action dated Sep. 27, 2016; Appln. No. 201410803896.7.
International Search Report and Written Opinion both dated Oct. 14, 2015; PCT/CN2015/084373.

* cited by examiner

SUBSTRATE INSPECTION DEVICE AND METHOD

FIELD OF THE INVENTION

The embodiments of the present invention relate to a substrate inspection device and method.

BACKGROUND

As well known, in display apparatus, substrates are often needed to be used. For example, in a LCD (Liquid Crystal Display) apparatus, an array substrate, a color film substrate, and so on are generally used. Thus, selection of the substrate is very important to the display apparatus. If the substrate is a defective product, the display apparatus can be failed during its operation. For this reason, generally, the substrate will be subjected to strict inspection before being put into market.

SUMMARY

The embodiments of the present invention provide a substrate inspection device and method to achieve effective inspection on a substrate which has a shape other than square shape.

At least one embodiment of the present invention provides a substrate inspection device, includes: a conveyance stage for carrying the substrate on its surface; a region scanning camera located at a first side of the conveyance stage, provided to be opposite to the surface, and configured to inspect standard specification of the substrate; a line scanning camera located at the first side of the conveyance stage, provided to be opposite to the surface, and configured to inspect edge line and size of the substrate; and a light source located at a second side of the conveyance stage opposite to the first side, configured to irradiate light rays onto the substrate, so as to be utilized by the region scanning camera and the line scanning camera for inspecting the substrate.

At least one embodiment of the present invention further provides a method for inspecting the substrate by using the substrate inspection device as above described, the method includes: loading the substrate onto the surface of the conveyance stage; inspecting the standard specification by using the region scanning camera; and inspecting the edge line and the size of the substrate by using the line scanning camera.

BRIEF DESCRIPTION OF THE DRAWINGS

In order to clearly illustrate the technical solution of the embodiments of the invention, the drawings of the embodiments will be briefly described in the following; it is obvious that the described drawings are only related to some embodiments of the invention and thus are not limitative of the invention.

DETAILED DESCRIPTION

In order to make objects, technical details and advantages of the embodiments of the invention apparent, the technical solutions of the embodiments will be described in a clearly and fully understandable way in connection with the drawings related to the embodiments of the invention. Apparently, the described embodiments are just a part but not all of the embodiments of the invention. Based on the described embodiments herein, those skilled in the art can obtain other embodiment(s), without any inventive work, which should be within the scope of the invention.

In study, the inventors of the present application noticed that a prior art apparatus for inspecting substrates generally can only inspect a substrate having square shape, and cannot inspect irregular shaped substrates having a shape other than square shape, therefore, the qualified rate of the irregular shaped substrates is significantly lowered.

Figure 1A:
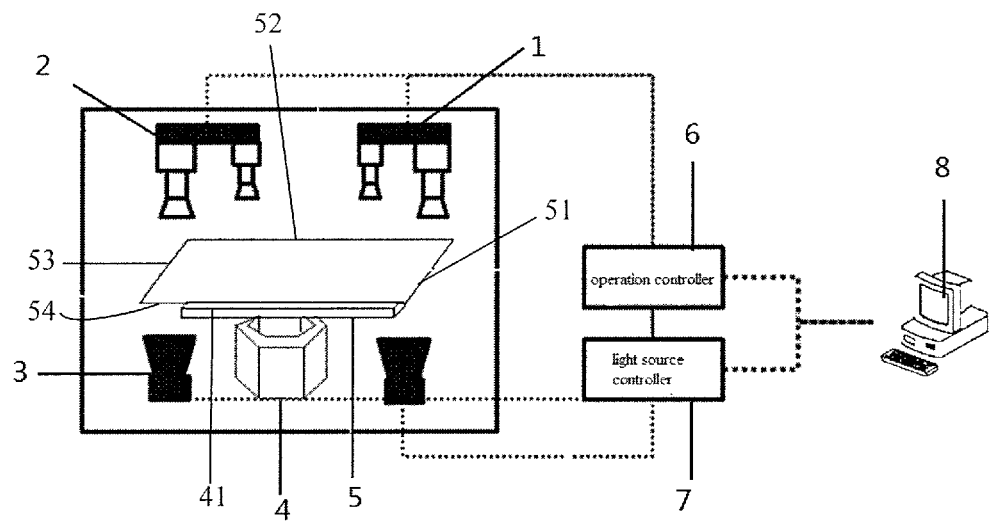
FIG. 1a is a schematic view showing a structure of a substrate inspection device provided by an embodiments of the present invention.

As shown in FIG. 1a, at least one embodiment of the present invention provides a substrate inspection device including a region scanning camera 1, a line scanning camera 2, a light source 3 and a conveyance stage 4.

In the substrate inspection device, the conveyance stage 4 is configured to carry the substrate 5 on its surface 41.

For example, the conveyance stage 4 can be a circular rotary worktable.

In the substrate inspection device, the region scanning camera 1 is located at a first side of the conveyance stage 4, opposite to the surface 41. The region scanning camera 1 is configured to inspect the substrate 5 for its standard specification, that is, to check whether or not the actual size of the substrate conforms the size of the substrate defined by the standard specification (e.g. lateral size, vertical size, and so on).

In the substrate inspection device, the line scanning camera 2 is located at the first side of the conveyance stage 2 and provided opposite to the surface 41. The line scanning camera 2 is configured to inspect edge lines (e.g. at least one of the edge lines 51, 52, 53 and 54) and size of the substrate 5.

In the substrate inspection device, the light source is located at a second side of the conveyance stage 4 face away from to the first side. The light source is configured to irradiate light rays onto the substrate 5, and the light rays are to be used by the region scanning camera 1 and the line scanning camera 2 for inspecting the substrate 5.

For example, the light source 3 can be a strobe light. Of course, the embodiments of the present invention are not limited thereby.

It is to be noted that the substrate inspection device provided by the embodiments of the present invention is suitable for inspecting any substrates having plate like structure, e.g. array substrates, color film substrates, touch substrates, and so on.

Figure 1B:
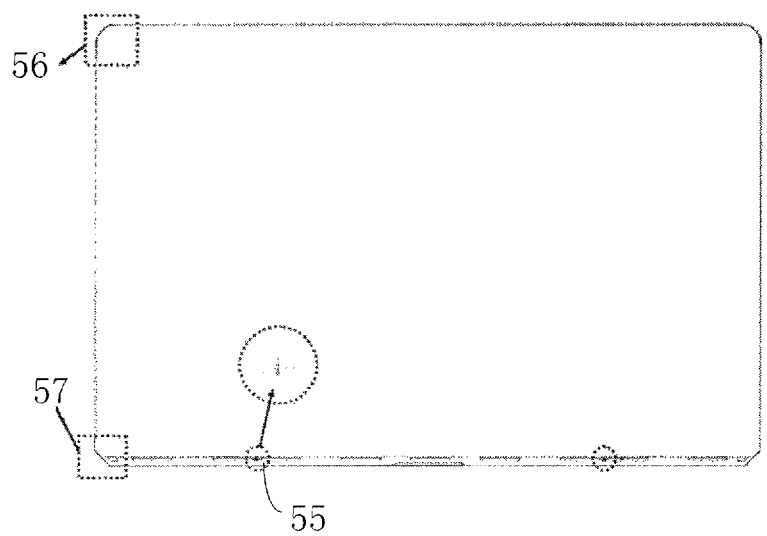
FIG. 1b is a schematic top view of a substrate.

According to at least one embodiment of the present invention, said inspecting the standard specification of the substrate 5 by the region scanning camera 1 includes: as shown in FIG. 1b, the region scanning camera 1 scans the substrate 5 for a calibration mark 55 (in FIG. 1b, a dashed-line circle shows an enlarged schematically structural view of the calibration mark 55) to obtain position coordinates of the calibration mark 55, scans the substrate for a circular region 56 (as shown by a arc portion in a dashed-line block in FIG. 1b) and/or a C-shaped cut region 57 (as shown by a folded line portion in another dashed-line block in FIG. 1b) to obtain data of the circular region 56 and/or the C-shaped cut region 57, and combines actual coordinates of the graphic design of the substrate 5, to inspect the standard specification of the substrate 5.

The substrate has various sizes. The graphic design of the substrate means the design diagrams of the various sizes of the substrate (e.g. CAD design diagrams, CAD files). In this design diagram, the position coordinates for respective portions of the substrate are shown.

According to at least one embodiment of the present invention, said inspecting the edge lines of the substrate 5 by the line scanning camera 2 includes inspecting the substrate 5 for burrs, cracks, notches, and determining whether or not the substrate 5 is qualified according to the inspection results.

According to at least one embodiment of the present invention, the substrate inspection device further includes a operation controller 6 for controlling the movement of the conveyance stage 4, the movement of the region scanning camera 1, and the movement of the line scanning camera 2.

According to at least one embodiment of the present invention, the substrate inspection device further includes a light source controller 7 for controlling light ray emitting of the light source 3.

According to at least one embodiment, the substrate inspection device further includes an user interface 8 configured for user's control of the operation of the substrate inspection device, such as, control of the operation of the operation controller 6 and the light source controller 7. In addition, the user interface 8 may also be used to provide the substrate inspection device with the data of the graphic design of the substrate by the user, and provide the user with the related images obtained by the region scanning camera 1 and the line scanning camera 2.

Figure 2:
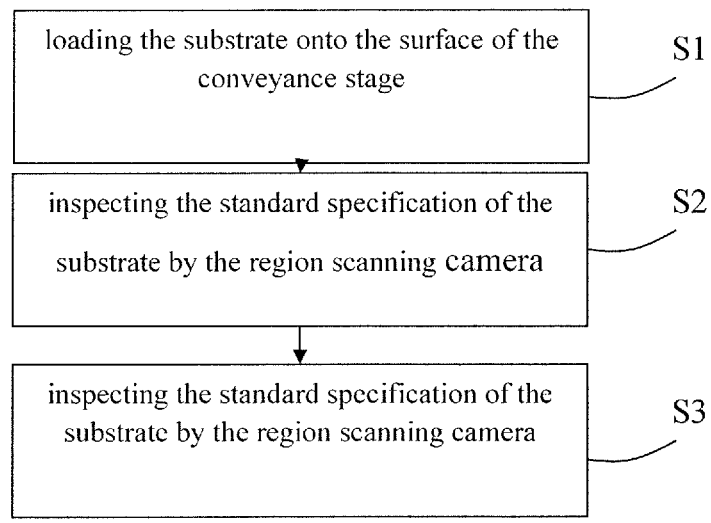
FIG. 2 is a schematic flowchart view showing a method of a substrate inspection method provided by an embodiments of the present invention.

As shown in FIG. 2, the at least one embodiment of the present invention provides a method for inspecting the substrate by using any one of the above substrate inspection devices. The method includes the steps of: S1, loading the substrate onto the surface of the conveyance stage; S2, inspecting the standard specification of the substrate by the region scanning camera; and S3, inspecting the edge lines and the size of the substrate by using the line scanning camera.

According to at least one embodiment of the present invention, the step S2 can include that the region scanning camera scans the substrate for the calibration mark to obtain position coordinates of the calibration mark; scans the substrate for the circular region and/or the C-shaped cut region to obtain data of the circular region and/or the C-shaped cut region; and combines actual coordinates of the graphic design of the substrate, so as to inspect the standard specification of the substrate.

Figure 3:
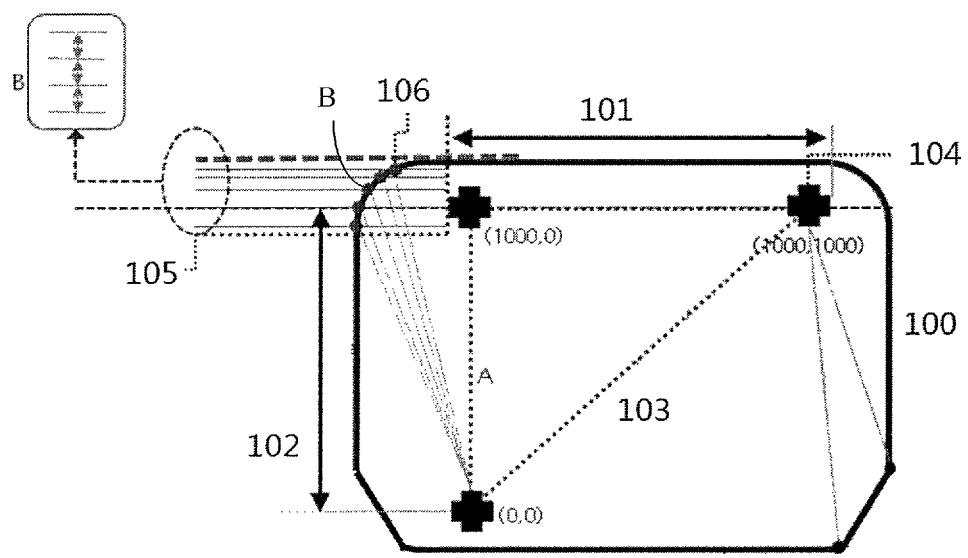
FIG. 3 is a schematic view showing measurement of a circle region and a C-shaped cut region of the substrate, as provided by an embodiments of the present invention.
Figure 4:
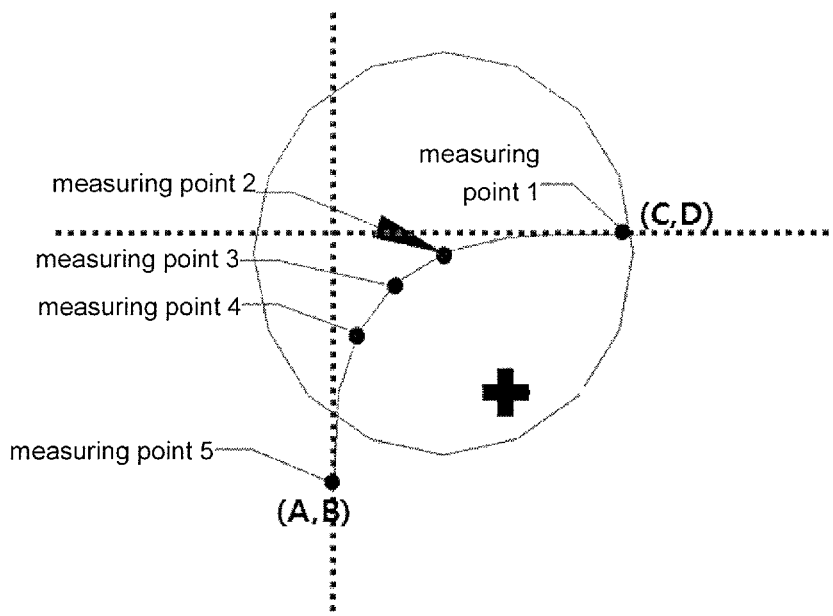
FIG. 4 is a schematic view showing measurement of the circle region of the substrate, as provided by the embodiments of the present invention.

As shown in FIG. 3 and FIG. 4, according to at least one embodiment of the present invention, measuring the circular region of the substrate can include the following step S211 to Step S215, which will be described in detail below.

Step S211: forming a reference line A for the calibration marks, by taking the calibration marks (as shown by the plus sign in FIG. 3) on the substrate (e.g. a glass substrate) as reference;

Step S212: then forming virtual lines 101 and 102 symmetrical to the reference line A;

Step S213: setting a circular region, i.e., line 106, as shown by the curve between the coordinate (A, B) and the coordinate (C, D) in FIG. 4, on the substrate by taking the line 105 as reference;

Step S214: making equidistant circular coordinate points B on the line 106 (that is, the circular coordinate points B are equally spaced along the direction of the line 106), by using the line 105 as the data of the coordinate location for logging on to a CAD software;

Step S215: after comparing the circular coordinate portions B with equidistant coordinate points in a circular region on a CAD design diagram, determining the circular region of the substrate.

It is to be noted that FIG. 3 is only a schematic view showing the principle for measuring the circular region and the C-shaped cut region on the substrate, the plus signs in FIG. 3 are not the actual calibration marks, and only indicate the position of the actual calibration marks on the actual substrate.

Figure 5:
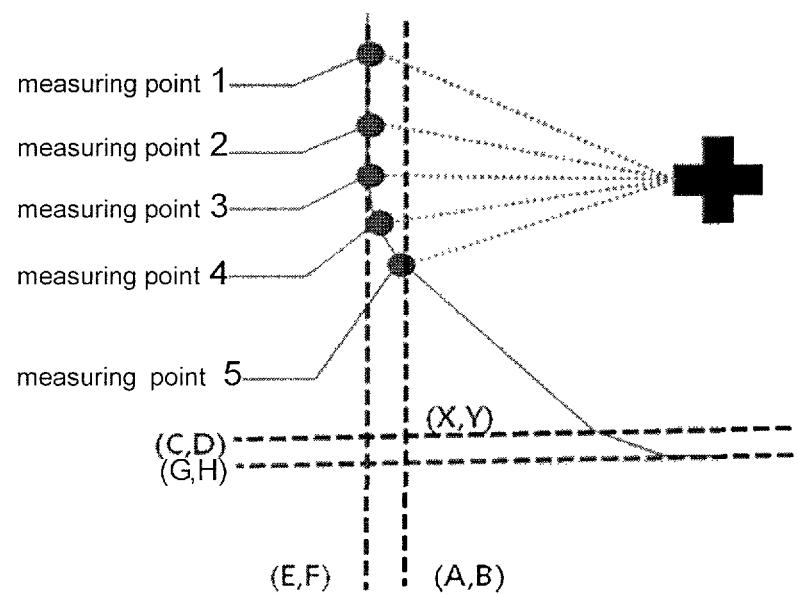
FIG. 5 is a schematic view showing measurement of the C-shaped cut region of the substrate, as provided by the embodiments of the present invention.

As shown in FIG. 3 and FIG. 5, according to at least one embodiment of the present invention, measuring the C-shaped region on the substrate can include the following step S221 to step S224, which will be described in detail below.

Step S221: setting (C, D) and (G, H) to make a beginning point and an end point of the measuring points 1~5 (i.e. measuring point 1 to measuring point 5);

The selected measuring points are points equidistantly dividing a portion of the C-shaped curve (as indicated by the curve on which the measuring points 1-5 are located, in FIG. 5) extending along a direction between the X direction and the Y direction, along a direction from the (C, D) to the underlying (G, H) (i.e. the direction from top to bottom in FIG. 5); In this case, the measuring coordinate points on the CAD design diagram are also the points equidistantly dividing the portion of the C-shaped curve extending in the direction between the X direction and the Y direction, along the direction from (C, D) to the underlying (G, H) on the CAD design diagram, as its measuring coordinate points.

Step S222: according to the curve selected from the diagram (as indicated by the curve on which the measuring points 1-5 are located in FIG. 5) and the perpendicular distance from a straight boundary (E, F) (indicating an edge of the substrate, but not indicating the actual edge of the actual substrate) to an inner side (as shown by the plus sign in FIG. 5) of the substrate, forming the (A, B) intersecting with the edge of the substrate by the displacement amount;

Step S223: according to the curve selected from the diagram and the perpendicular distance from a straight boundary (G, H) (indicating another edge of the substrate, but not indicating the actual edge of the actual substrate) to the inner side of the substrate, forming the (C, D) intersecting with the edge of the substrate by the displacement amount;

Step S224: beginning calculation from an intersection point (X, Y) of the (A, B) and the (C, D), determining distances from the plus sign to the respective measuring points 1~5.

In the present embodiment, in the case that the calibration mark on the substrate are indicated by the plus sign in FIG. 5 for determining the coordinates of the measuring points 1~5, the plus sign is used as a reference point, and base on this reference point, the distances from the coordinates of the respective measuring points to the reference points are obtained and further compared with data read from the CAD software, to calculate the difference between the actual object (i.e. the actual substrate, that is, the image of the substrate obtained by the region scanning camera) and the design diagram (that is, the graphic design of the substrate).

According to at least one embodiment of the present invention, the step S3 can include inspecting the substrate for burrs, cracks, notches, and determining whether or not the substrate is qualified according to the inspection result.

It is to be noted that the order of the above step S2 and the step S3 can be exchanged.

Figure 6:
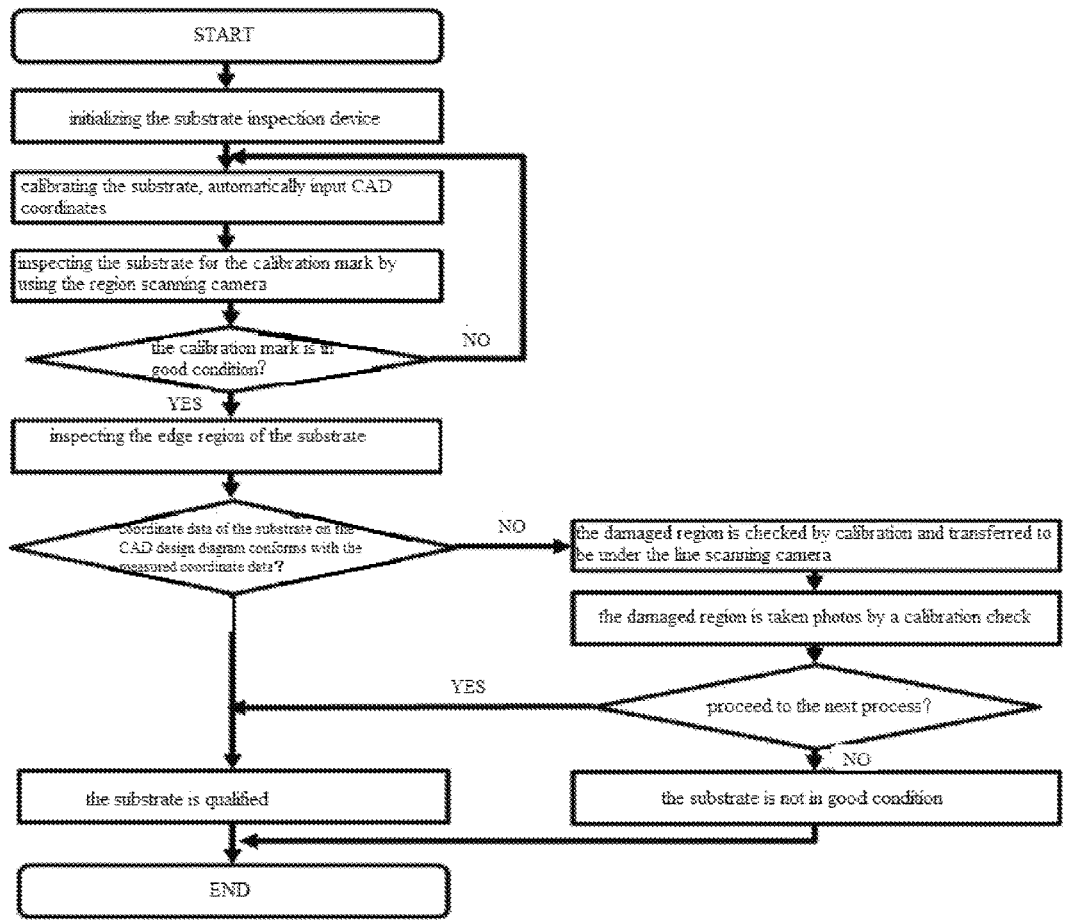
FIG. 6 is a schematic flowchart view showing a practical operation of the substrate inspection method provided by the embodiments of the present invention.

As shown in FIG. 6, an application flowchart for inspecting the substrate by using the substrate inspection device in the practical operation will be described in detail, for example, the application flowchart can include the following step S01 to step S08, which will be described in detail below.

Step S01: beginning to inspect the substrate (e.g. a glass substrate);

Step S02, initializing the substrate inspection device;

Step S03: calibrating the substrate, in this step, the coordinates being input automatically by the CAD software;

In this step, the CAD software is designed to have a function of automatically setting inspection data after the main inspection device is turned on.

Step S04: inspecting the substrate for the calibration mark by using the region scanning camera. In this step, it is necessary to use a vision alignment function of the region scanning camera;

Step S05: inspecting whether or not the calibration mark is in good condition;

Step S06: if the calibration mark is in good condition, inspecting the edge region of the substrate by using the line scanning camera. In this step, a function for comparing the CAD design data obtained by applying symmetrical algorithm with the data on the actually captured image is used;

Step S07: determining whether or not the coordinate data of the substrate on the CAD design diagram conforms with the measured coordinate data, if yes, it is determined that the substrate is qualified; and Step S08: the inspection is ended.

In this flowchart, in the step S05, if the calibration mark is not in good condition, the process returns to Step S03.

In the step S07, if the substrate is not qualified (that is, the coordinate data of the substrate on the CAD design diagram does not conform with the measured coordinate data), then the damaged region is checked by using calibration line and transferred to be under the line scanning camera, so that the damaged region is taken photos by a calibration check lens to determine whether or not proceed to the next process: if yes, proceed to the process for determining the state of the substrate, and if no, it is determined that the substrate is not in good condition, and proceed to step S08, the inspection is ended.

According to the substrate inspection device and method provided by the embodiments of the present invention, the substrate in various specification can be inspected, especially for the substrate with irregular shape, thus it is possible to accurately determine the unqualified substrate.

The present disclosure has been described above by way of the exemplary embodiment, and the protection scope of the present disclosure would not be limited therein, and is only defined by the following claims.

The present application claims the priority of a Chinese Patent Application No. 201410803896.7, filed on Dec. 18, 2014, the disclosure of which is entirely incorporated herein by reference.

What is claimed is:

1. A substrate inspection device including:
   a conveyance stage for carrying the substrate on its surface;
   a region scanning camera located at a first side of the conveyance stage, provided to be opposite to the surface, and configured to inspect standard specification of the substrate;
   a line scanning camera located at the first side of the conveyance stage, provided to be opposite to the surface, and configured to inspect edge line and size of the substrate; and
   a light source located at a second side of the conveyance stage opposite to the first side, configured to irradiate light rays onto the substrate, so as to be utilized by the region scanning camera and the line scanning camera for inspecting the substrate,
   wherein, the region scanning camera is configured to check whether or not an actual size of the substrate conforms a size of the substrate defined by a standard specification.

2. The device according to claim 1, wherein the line scanning camera configured for inspecting the edge line of the substrate includes:
   the line scanning camera configured for inspecting the substrate for burrs, cracks, notches, and determining whether or not the substrate is in good condition according to the inspection result.

3. The device according to claim 2, further including:
   an operation controller configured for controlling movement of the conveyance stage, movement of the region scanning camera and movement of the line scanning camera.

4. The device according to claim 2, further including:
   a light source controller configured for controlling light ray emitting of the light source.

5. The device according to claim 1, further including:
   an operation controller configured for controlling movement of the conveyance stage, movement of the region scanning camera and movement of the line scanning camera.

6. The device according to claim 5, further including:
   a light source controller configured for controlling light ray emitting of the light source.

7. The device according to claim 1, further including:
   a light source controller configured for controlling light ray emitting of the light source.

8. A method for inspecting a substrate by using the substrate inspection device according to claim 1, including:
   loading the substrate onto the surface of the conveyance stage;
   inspecting the standard specification by using the region scanning camera and checking whether or not an actual size of the substrate conforms a size of the substrate defined by a standard specification; and
   inspecting the edge line and the size of the substrate by using the line scanning camera.

9. The method according to claim 8, wherein the inspecting the edge lines of the substrate by using the line scanning camera includes:
   inspecting the substrate for burrs, cracks, and notches, and determining whether or not the substrate is in good condition according to the inspection result.

10. A method for inspecting a substrate by using the substrate inspection device according to claim 1, including:
  loading the substrate onto the surface of the conveyance stage;
  inspecting the standard specification by using the region scanning camera; and
  inspecting the edge line and the size of the substrate by using the line scanning camera, wherein, the inspecting the standard specification of the substrate by using the region scanning camera includes:
  the region scanning camera obtains position coordinates of calibration marks by scanning the substrate for the calibration marks; obtains data of at least one of a circular region or a C-shaped cut region by scanning the substrate for the at least one of the circular region or the C-shaped cut region; and combines actual coordinate of graphic design of the substrate to inspect the standard specification of the substrate.

11. The method according to claim 10, wherein the inspecting the edge lines of the substrate by using the line scanning camera includes:
  inspecting the substrate for burrs, cracks, and notches, and determining whether or not the substrate is in good condition according to the inspection result.

12. A substrate inspection device including:
  a conveyance stage for carrying the substrate on its surface;
  a region scanning camera located at a first side of the conveyance stage, provided to be opposite to the surface, and configured to inspect standard specification of the substrate;
  a line scanning camera located at the first side of the conveyance stage, provided to be opposite to the surface, and configured to inspect edge line and size of the substrate; and
  a light source located at a second side of the conveyance stage opposite to the first side, configured to irradiate light rays onto the substrate, so as to be utilized by the region scanning camera and the line scanning camera for inspecting the substrate, wherein the region scanning camera configured for inspecting the standard specification of the substrate includes:
  the region scanning camera configured for obtaining position coordinate of a calibration mark by scanning the substrate for the calibration mark; obtaining data of at least one of a circular region or a C-shaped cut region by scanning the substrate for the circular region and/or the C-shaped cut region; and by combining actual coordinate of graphic design of the substrate to inspect the standard specification of the substrate.

13. The device according to claim 12, wherein the line scanning camera configured for inspecting the edge line of the substrate includes:
  the line scanning camera configured for inspecting the substrate for burrs, cracks, notches, and determining whether or not the substrate is in good condition according to the inspection result.

14. The device according to claim 12, further including:
  an operation controller configured for controlling movement of the conveyance stage, movement of the region scanning camera and movement of the line scanning camera.

15. The device according to claim 12, further including:
  a light source controller configured for controlling light ray emitting of the light source.

* * * * *